US011020263B2

United States Patent
Clough

(10) Patent No.: US 11,020,263 B2
(45) Date of Patent: Jun. 1, 2021

(54) REVERSE INSOLE

(71) Applicant: Cluffy, LLC, Polson, MT (US)

(72) Inventor: James Clough, Polson, MT (US)

(73) Assignee: Cluffy, LLC, Polson, MT (US)

(*) Notice: Subject to any disclaimer, the term of this patent is extended or adjusted under 35 U.S.C. 154(b) by 0 days.

(21) Appl. No.: 15/988,517

(22) Filed: May 24, 2018

(65) Prior Publication Data
US 2018/0338854 A1 Nov. 29, 2018

Related U.S. Application Data

(60) Provisional application No. 62/510,810, filed on May 25, 2017.

(51) Int. Cl.
| | |
|---|---|
| *A61F 5/14* | (2006.01) |
| *A43B 7/14* | (2006.01) |
| *A43B 17/02* | (2006.01) |
| *A43B 7/22* | (2006.01) |

(52) U.S. Cl.
CPC ............... *A61F 5/14* (2013.01); *A43B 7/145* (2013.01); *A43B 17/023* (2013.01); *A43B 7/223* (2013.01)

(58) Field of Classification Search
CPC ......... A43B 7/14; A43B 7/1405; A43B 7/141; A43B 7/1415; A43B 7/1445
USPC ........................................................ 36/145
See application file for complete search history.

(56) References Cited

U.S. PATENT DOCUMENTS

| | | | | |
|---|---|---|---|---|
| 1,477,750 A | * | 12/1923 | Endrea ..................... | A43B 7/14 36/178 |
| 2,221,202 A | * | 11/1940 | Ratcliff ................... | A43B 7/142 36/155 |
| 2,729,900 A | * | 1/1956 | Maccarone .............. | A43B 7/14 36/58.5 |
| 3,084,695 A | * | 4/1963 | O'Donnell ............. | A43B 7/143 36/174 |
| 4,317,293 A | * | 3/1982 | Sigle ....................... | A43B 7/22 36/43 |
| 4,541,184 A | * | 9/1985 | Leighton ................ | A43B 7/144 36/178 |

(Continued)

OTHER PUBLICATIONS

"Fixed", Merriam-Webster, https://www.merriam-webster.com/dictionary/fixed (last visited May 7, 2020).*

(Continued)

*Primary Examiner* — Alissa L Hoey
*Assistant Examiner* — Patrick J. Lynch
(74) *Attorney, Agent, or Firm* — Osha Bergman Watanabe & Burton LLP

(57) ABSTRACT

An orthopedic insole is provided with an insole having a bottom portion for facing a sole of a shoe; one or more orthopedic pads disposed on the bottom portion of the insole at one or more judiciously selected locations to provide different heights and/or different physical properties. An orthopedic shoe is also provided having an upper; a sole attached to the upper, and the removable insole within the shoe. An orthopedic insole is provided with an insole having a bottom portion for facing a sole of a shoe; a first orthopedic pad disposed on the bottom portion of the insole at a location corresponding to at least one selected from the group consisting of a medial longitudinal arch, a lateral longitudinal arch, and a transverse metatarsal arch of a foot.

17 Claims, 6 Drawing Sheets

(56) References Cited

U.S. PATENT DOCUMENTS

| | | | |
|---|---|---|---|
| 4,813,157 A * | 3/1989 | Boisvert | A43B 7/142 36/145 |
| 5,901,394 A * | 5/1999 | Greenawalt | A43B 3/128 12/142 N |
| 6,170,176 B1 * | 1/2001 | Clough | A43B 7/145 36/117.5 |
| 6,205,685 B1 * | 3/2001 | Kellerman | A43B 1/0072 36/160 |
| 6,874,258 B2 | 4/2005 | Clough et al. | |
| 6,938,363 B1 | 9/2005 | Clough | |
| D536,518 S * | 2/2007 | Gallegos | D2/961 |
| 7,681,333 B2 * | 3/2010 | Dardinski | A43B 3/26 36/100 |
| 8,453,346 B2 * | 6/2013 | Steszyn | A43B 7/142 36/146 |
| 2004/0194344 A1 * | 10/2004 | Tadin | A43B 7/141 36/44 |
| 2011/0289802 A1 * | 12/2011 | Clough | A61F 5/14 36/140 |
| 2012/0246971 A1 * | 10/2012 | Donzis | A43B 7/1425 36/43 |
| 2014/0059885 A1 * | 3/2014 | Patchett | A43B 17/03 36/44 |
| 2016/0227879 A1 * | 8/2016 | Haselaars | A43B 7/141 |
| 2017/0245593 A1 * | 8/2017 | Kilgore | A43B 17/18 |
| 2018/0098598 A1 * | 4/2018 | Warner | A43B 3/108 |

OTHER PUBLICATIONS

"Why a Custom Footbed?", Lathrop and Sons, Home (https://lathropandsons.com/) (3 pages).

"Custom Footbeds High Country Synergy Footbeds", Lathrop and Sons, Home (https://lathropandsons.com/), L&S Synergy Footbeds (https://lathropandsons.com/synergy-footbeds.html), High Country Synergy Footbeds (3 pages).

* cited by examiner

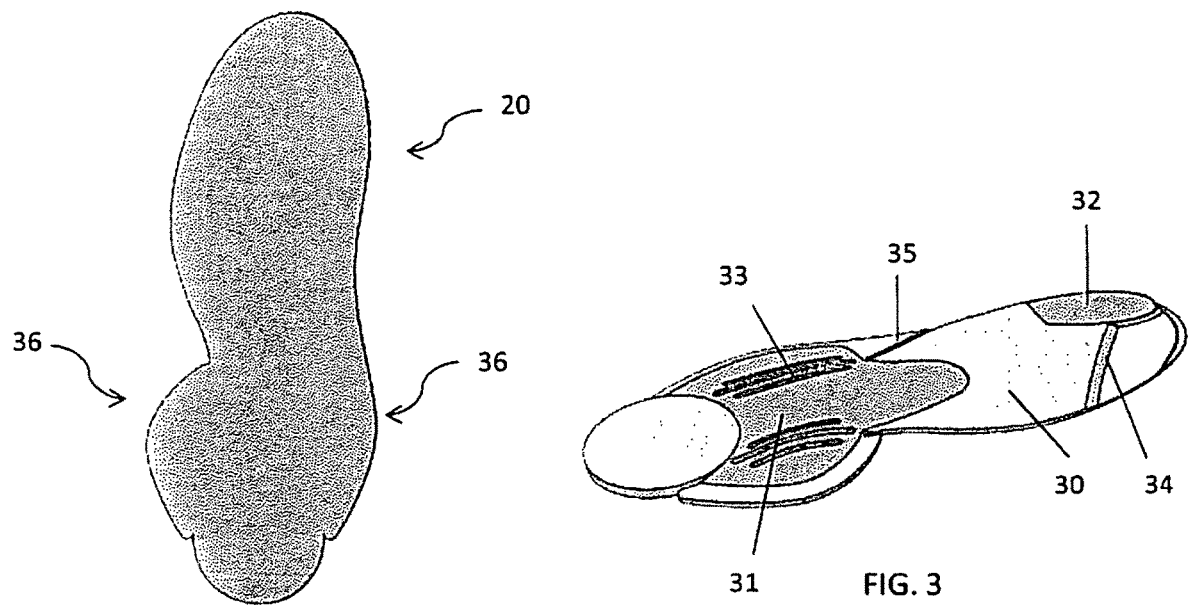
FIG. 2
FIG. 3
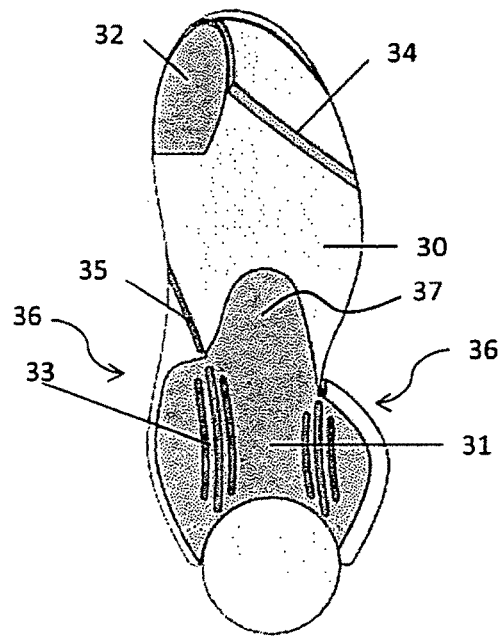
FIG. 4

REVERSE INSOLE

BACKGROUND

Technical Field

Embodiments disclosed herein relate generally to orthopedic devices, particularly to therapeutic insoles with contoured surfaces on the bottom designed to account for the change in the foot that occurs at different phases of the gait cycle.

Background Art

When a person ambulates or walks, the foot first lands in a supinated position and then moves to a more pronated position to absorb the shock of contacting the ground. The pronated phase is followed by a final supinated phase, in which the foot pushes off into the next stride. In the pronation phase, the foot contacts the ground, and then the arch lowers and acts as the body's shock absorber. In the supination phase, as the big toe moves upward, the arch height is restored and the bones in the foot form a rigid structure to push off into the next step.

Pronation involves a tri-plane rotation of a joint or part in a forward direction or toward the midline of the body, while supination involves rotation of a joint or part in an outward direction or away from the midline of the body. When a person over-pronates or places too much force on the inside of a foot, or over supinates in the early part of stance and puts too much strain on the outside of the foot, the foot functions abnormally and puts strain on the medial and/or lateral longitudinal arches. A foot that stays pronated throughout the walking stance is inefficient at propelling the body forward. The instability resulting from over-pronation can lead to arch, foot, ankle, and/or leg pain, as well as postural problems due to excessive internal rotation of the leg. A foot that stays excessively supinated or inverted may also result in instability in propulsion. To propel the body forward in an efficient manner, the foot would stabilize in propulsion by rolling through the big toe and engaging the windlass mechanism through tensioning of the the plantar fascia. If the body weight is on the lateral arch prematurely in midstance, the foot will also not properly stabilize as the big toe will not extend properly and stabilize the foot through the windlass mechanism. It is critical then to support both the medial and lateral arches in order for the foot to properly re-stabilize through propulsion by extending the big toe and engaging the windlass mechanism.

Footwear may be designed to help correct improper pronation and supination. Different biomechanical theories have been proposed and adopted to improve the functional aspects of footwear. For example, U.S. Pat. Nos. 6,170,176, 6,874,258, and 6,938,363, issued to the inventor of the present invention, disclose shoe appliances, sold under the trade name of Cluffy Wedge®, that are effective in treating foot problems related to functional hallux limitus, first-ray insufficiency, and an unstable windlass mechanism.

While orthopedic shoes and soles are effective in most situations for correcting improper pronation and supination, there is no such design that accounts for the change in the foot that occurs at different phases of the gait cycle.

The present invention relates to a foot insole, with a flat surface against the foot and a contoured surface on the bottom against the shoe. The materials used in construction of this device will deform when weight is applied, pushing the material up against the foot, allowing correction and support to be applied to the foot, when it is needed most during the phases of gait when the foot is fully loaded at heel contact and mid stance. The insole will tend to rebound away from the foot as weight bearing under the foot arches is reduced in propulsion. During propulsion, as the big toe moves upward, less correction is needed under the foot, as the foot naturally stabilizes itself through the windlass mechanism.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments of the present disclosure are directed to an orthopedic insole, comprising: an insole having a bottom portion for facing a sole of a shoe; one or more orthopedic shaped pads disposed on the bottom portion of the insole at one or more locations selected from the group consisting of a location under a big toe, a location under second and third metatarsals, and fourth and fifth metatarsals, a location under a medial longitudinal arch, a location under a lateral longitudinal arch, a location under a transverse metatarsal arch, and a location under a heel.

In another aspect, embodiments of the present disclosure are directed to an orthopedic insole, comprising: an insole having a bottom portion for facing a sole of a shoe; a first orthopedic shaped pad disposed on the bottom portion of the insole at a location corresponding to at least one selected from the group consisting of a medial longitudinal arch, a lateral longitudinal arch, and a transverse metatarsal arch of a foot.

In another aspect, embodiments of the present disclosure are directed to a shoe, comprising: an upper; a sole attached to the upper, and a removable insole within the shoe, the removable insole having: a bottom portion that faces the sole of the shoe; and one or more orthopedic shaped pads disposed on the bottom portion of the insole at one or more locations selected from the group consisting of a location under a big toe, a location under second and third metatarsals, and fourth and fifth metatarsals, a location under a medial longitudinal arch, a location under a lateral longitudinal arch, a location under a transverse metatarsal arch, and a location under a heel.

Other aspects and advantages of the claimed subject matter will be apparent from the following description and the appended claims.

BRIEF DESCRIPTION OF DRAWINGS

FIG. 2 is a schematic illustrating the top view of the orthopedic insole.

FIG. 3 is a schematic illustrating the isometric view of the orthopedic insole.

FIG. 4 is a schematic illustrating the bottom view of the orthopedic insole.

DETAILED DESCRIPTION

Embodiments of the present disclosure relate to orthopedic insoles and methods for improving stability of a foot during standing and/or ambulation.

In one aspect, embodiments disclosed herein relate to an orthopedic insole in accordance with one embodiment of the disclosure includes an insole having a bottom portion; and one or more orthopedic pads disposed on the bottom portion of the insole. In this description, a location under a particular foot structure is meant a location in the bottom of the orthopedic insole that would be under that particular structure of the foot when the orthopedic insole is worn in a normal fashion. The one or more orthopedic pads may be placed at judiciously selected locations in the bottom of the orthopedic insole to provide different heights, contours, and/or different physical properties (e.g., flexibility, density, and/or durometer). The orthopedic pads, which may be made of materials having different flexibilities, densities, and/or durometers, can allow different parts of a foot to flex to different extents relative to the neighboring regions of the foot. Further, by being located on the bottom of the insole (facing the shoe sole), rather than an upper surface of the insole (facing the foot), the insole will provide correction and support to the foot to the stages of ambulation when it is needed most and will rebound away from the foot during the other stages when less correction is needed. These relative flexibilities may help to alleviate stress and/or pain during standing or ambulation, thereby improving normal function of a foot.

Figure 1:
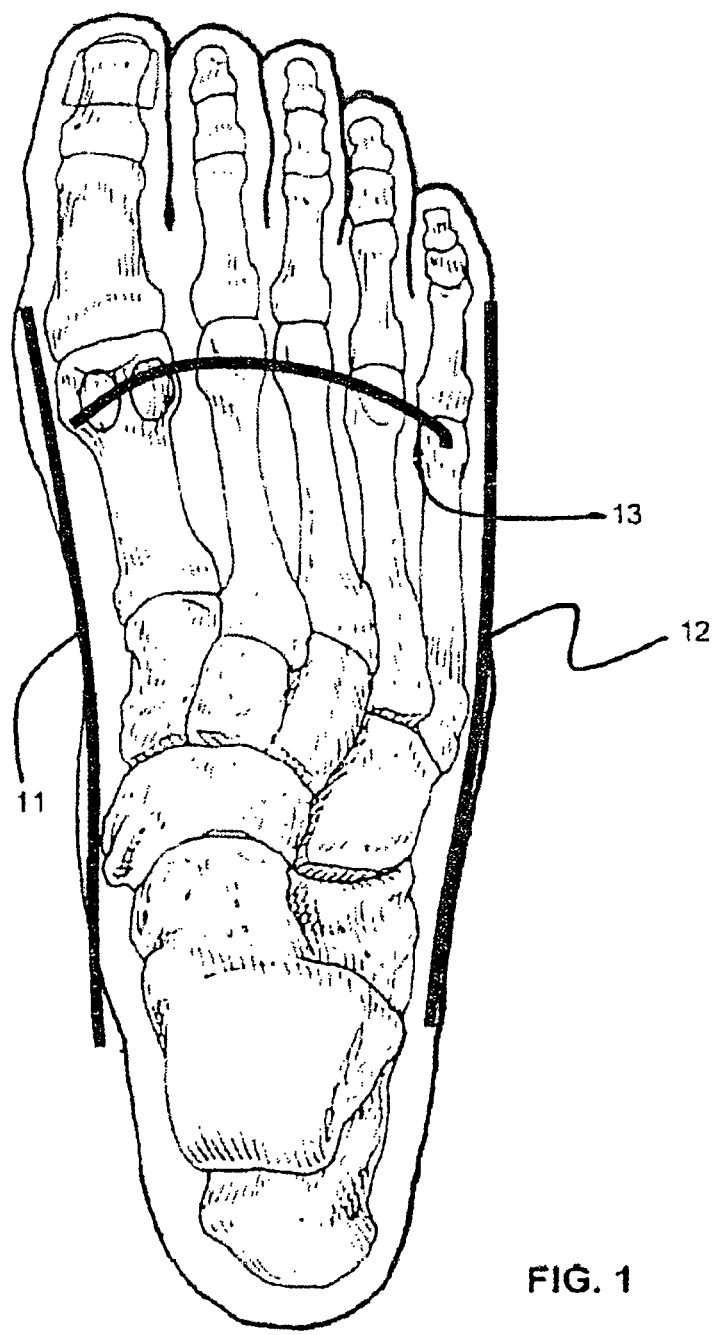
FIG. 1 is a schematic illustrating bones of a foot, including various arches formed by these bones.

FIG. 1 shows a schematic of a foot, illustrating various bone structures. Also illustrated in FIG. 1 are the various arches: the medial longitudinal arch 11, the lateral longitudinal arch 12, and the transverse/metatarsal arch 13. These arches allow the foot to change from a shock absorber at initial contact with the weight bearing surface, (flattening of the arches), to a supinator, or rigid structure, (higher arch) as the foot moves forward and prepares the body for forward movement. Movement of the big toe upward primarily causes the realignment of the bone structure to allow this change in foot shape to occur. Any interruption of this normal change in foot structure may result in inefficient ambulation, pain, and/or injury.

The needs of the foot change depending on the phase of the gait cycle. As the foot contacts the ground, it naturally pronates to absorb shock and allow the foot to adapt to the terrain. When the pronation becomes excessive, support to prevent this excessive movement is advantageous. As the foot moves forward and the big toe moves upward, this support is not necessary as the foot naturally stabilizes itself through the windlass mechanism. This allows the foot to assume a closed-packed position and become very stable, so it effectively propels the body forward for the next step. As the big toe moves upward, there is a bow stringing effect in the plantar fascia (the ligament that connects the heel bone to the toes). For conventional insoles providing support from the upper surface of the insole, the plantar fascia may rub against the arch support provided by the insole during this stage of gait. Thus, the inventor of the present disclosure has found that by providing the support on the bottom surface of the insole, the insole may rebound away from the foot and reduce the amount or extent of irritation experienced by the plantar fascia as the heel pushes upwards (and the big toe bends).

Figure 5:
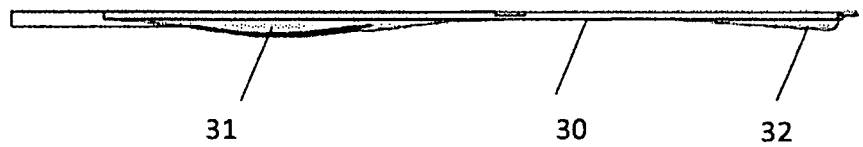
FIG. 5 is a schematic illustrating the side view of the orthopedic insole.
Figure 6:
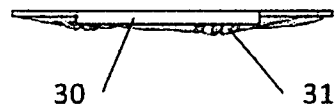
FIG. 6 is a schematic illustrating the back view of the orthopedic insole.
Figure 7:
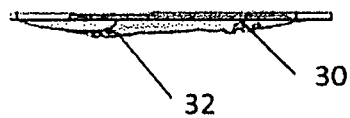
FIG. 7 is a schematic illustrating the front view of the orthopedic insole.
Figure 8:
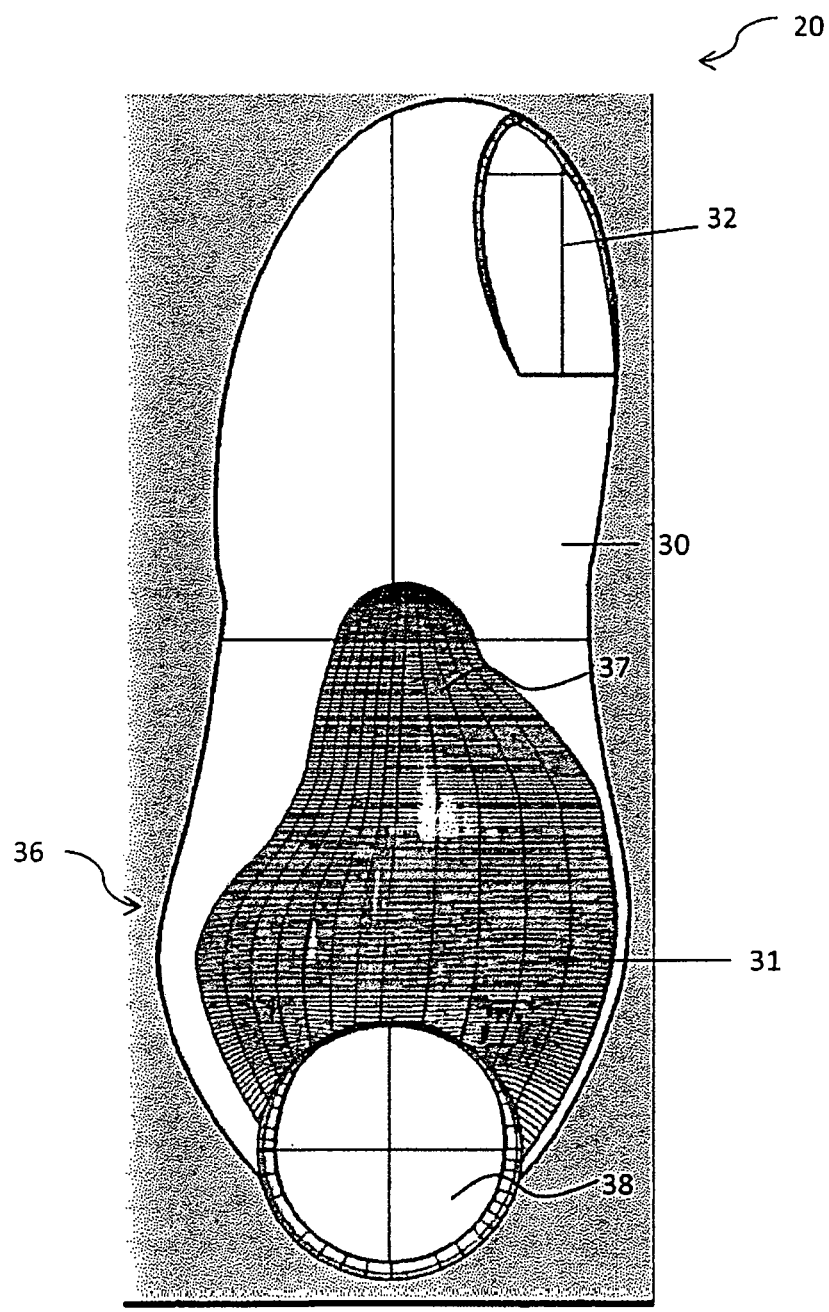
FIG. 8 is a schematic showing bottom pads on an orthopedic insole.
Figure 9:
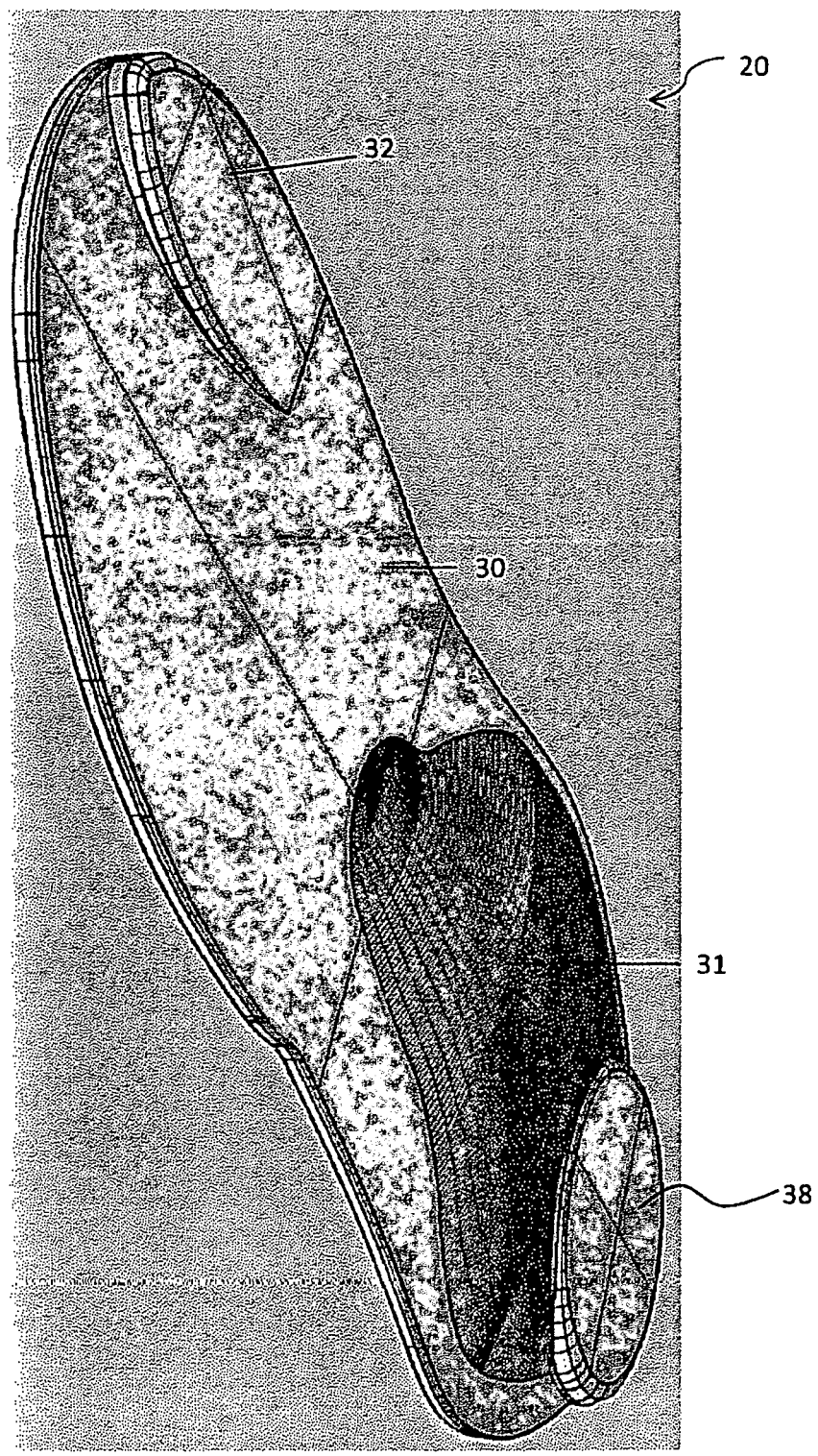
FIG. 9 is a schematic showing an isometric view of the orthopedic insole
Figure 10:
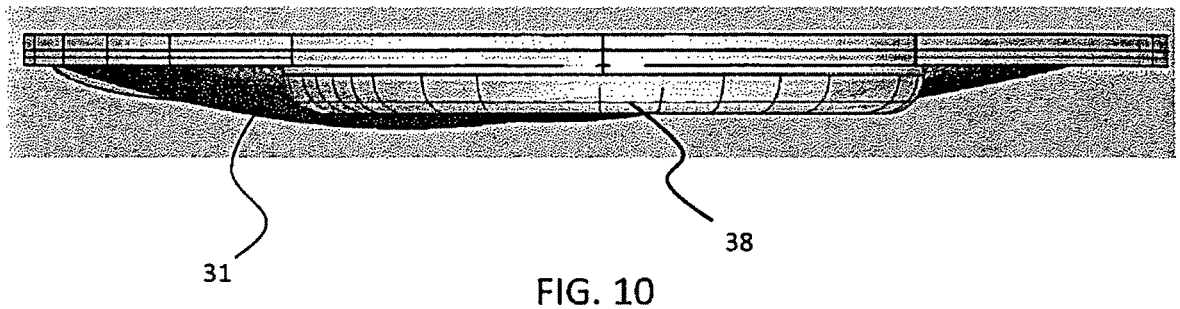
FIG. 10 is a schematic showing a back view of the orthopedic insole.
Figure 11:
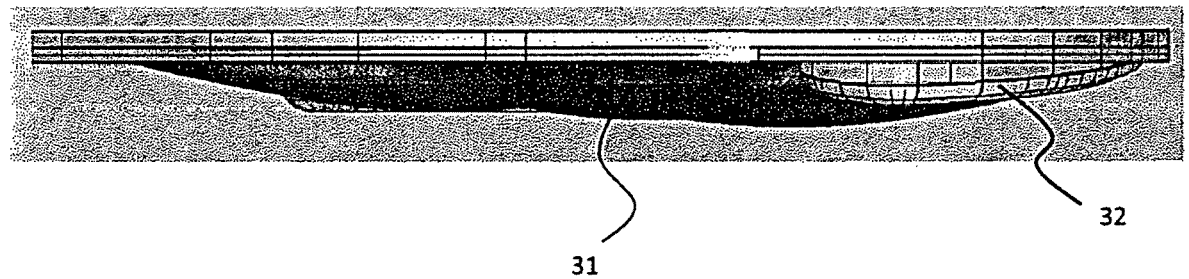
FIG. 11 is a schematic showing a side view of the orthopedic insole.

Thus, embodiments of the disclosure relate to orthopedic insoles having orthopedic pads shaped to contour to the normal shape of the foot in its neutral position disposed on the bottom portion thereof at judicially selected locations to correct for imperfections in foot function. FIGS. 2-7 show a schematic illustrating several orthopedic shaped pads at selected locations disposed on the bottom portion of the insole 20. As shown, in this example, there are two orthopedic pads: the orthopedic pad 31 disposed at the location under an arch, and the orthopedic pad 32 disposed at the location under a big toe. FIG. 2 shows the top view of the orthopedic insole. FIG. 3 shows the isometric view of the orthopedic insole. FIG. 4 shows the bottom view of the orthopedic insole. FIG. 5 shows the side view of the orthopedic insole. FIG. 6 shows the back view of the orthopedic insole. FIG. 7 shows the front view of the orthopedic insole. FIG. 8 shows another perspective view of the bottom of the insole. FIG. 9 shows another perspective view of the bottom of the insole. FIG. 10 shows another view from the back of the insole. FIG. 11 shows another view of the side of the insole.

Further, while FIGS. 2-11 show the pads 31 and 32 extending a height away from the bottom surface of the insole, it is envisioned that in one or more embodiments, the pad 32 under the big toe may instead extend away from an upper surface of the insole (shown in FIG. 2), rather than a bottom surface, while the pad 31 under the arch(es) extends away from the bottom surface.

Different orthopedic pads at different locations are designed to provide different functions. For example, an orthopedic pad under the big toe can help elevate (extend) the big toe relative to the remaining toes and the metatarsal bones. When one walks or runs, the big toe provides propulsion force and the big toe is supposed to dorsiflex between 50 and 90 degrees. If the big toe cannot extend in this manner, the body will compensate by moving in an abnormal manner, resulting in abnormal motion of the body, initiated by abnormal function of the foot. This can cause abnormal motion of the lower extremity joints, and resulting postural deficiencies and soft tissue strain. Ultimately this impairs normal function and results in pain, and/or deformity. By having an orthopedic pad under the big toe, one can potentially prevent hallux rigidus from developing which results in loss of motion in the big toe (i.e., metatarsal phalangeal joint). Thus, an orthopedic pad under the big toe may facilitate unrestricted motion of the big toe during gait by positioning the medial and lateral collateral ligaments in a parallel orientation to the ground. Advantages of such proper big toe motion include: 1) engagement of the windlass mechanism to provide better stability to the human foot, 2) improved first metatarsal head weight bearing and redistributing forces on the ball of the foot, and/or (3) improved sagittal plane motion of the big toe (and therefore of the ankle, knee, hip, and back) when ambulating. Further, by having an orthopedic pads under the big toe, one can alleviate the condition of hallux limitus, which results from loss of motion in the big toe joint (i.e., metatarsophalangeal joint).

Orthopedic pads under metatarsal heads 2-3 can be used to provide additional cushioning under these bones. These bones do not normally bear the majority of the forefoot weight individually. When abnormal foot function occurs, they can become quite sore from abnormal weight distribution. Further, orthopedic pads under metatarsal heads 2-3 can be used to provide additional weight redistribution to the second and third metatarsophalangeal joints.

Similarly, by having orthopedic pads shaped to contour to the normal arch configuration under one or more of the arches of a foot, one can correct over pronation, in which the arches lower too much. For example, the medial longitudinal arch absorbs the majority of the shock of impact while walking, jumping or running. Therefore, an orthopedic pad placed under the medial longitudinal arch may be selected for its ability to control the deformation of the arch with weight bearing ambulation. Pad 31 extends to form an arch support on the lateral longitudinal arch 37, which will have the ability to prevent over supination from structural deformity causing an individual to walk on the outside of the foot, or as a result of the medial arch pushing the foot laterally, causing the foot to abnormally supinate. The orthopedic pad under the arch may be designed to facilitate support of the foot through the midtarsal joint and allow stabilization of the midfoot so the ankle and first metatarsal phalangeal joint can move better as needed for normal ambulation. The orthopedic pad under the arch may be designed to facilitate support of the foot through the midfoot joints and allow stabilization of these joints so other joints that need to move can move better. This pad may go up the foot (wrapping around the foot) on the medial side and/or the lateral side of the foot to provide additional support to the foot structure in the transverse plane. Since pronation and supination are tri-plane motions, the insole is designed to control the motion of the foot in all three planes of motion. Advantages of midfoot support may include: (1) To slow down abnormal pronation and supination movement of the foot to promote a more normal neutral alignment of the foot structure. When these movements become excessive, they can cause abnormal strain on the arch ligaments and tendons that provide support of the arches of the foot such as the posterior tibial tendon, peroneal tendons, plantar fascia and spring ligament. By promoting a more neutral alignment of the foot, the insole may assist in allowing proper timing of pronation and supination and allow better physiologic motion of the foot, ankle and suprastructure during ambulation; and (2) allowing the foot to have total contact allows better proprioceptive feedback through the nociceptors of the skin for enhanced balance and position sense.

Further, an orthopedic pad under the heel (i.e., heel plugs or heel lifts) may elevate the heel of the foot to allow for less strain of the Achilles tendon and plantar fascia. This pad may thus be used when there is abnormal shortening of the Achilles tendon from chronic malfunction of the foot and ankle. This lack of motion of the ankle is often a result of excessive motion of the midfoot during ambulation. The most commonly manifestion of this is mechanically induced heel pain or plantar fasciitis, a very common malady of the foot. Further, it is also envisioned that one can provide cushion to the heel to minimize the impact when the foot hits the ground, as a result of walking on unforgiving surfaces.

As noted above, an orthopedic insole in accordance with embodiments of the disclosure may include one or more of the orthopedic shaped pads at one or more of these locations. When more than one orthopedic shaped pads are used, one may achieve a synergistic effect—i.e., that are not achievable by individual pads. Conventionally, such "pads" would be located on the upper surface of the insole, to directly interface the foot when used in a shoe. However, in accordance with the present disclosure, one or more pads may be located on the reverse or bottom side of the insole, facing the sole of the shoe, rather than the foot. By facing away from the foot rather than towards the foot, during the ambulation process, the insole may dynamically support the foot. That is, a region of the insole that supports the foot during one phase of ambulation has a different or no effect during a different phase. For example, a pad in one or more of the arches described above may support the arch(es) during initial heel strike and foot flattening, but once the heel lifts off the ground (and the big toe bends relative to the rest of the foot), the insole does not provide the same constant contact with the arch(es).

Referring back to FIGS. 2 and 5-11, the upper surface of the insole is substantially flat. Rather the orthopedic pads 31 on the bottom surface 30 of the insole may provide a contoured surface to provide the necessary support to the various regions of the foot described above upon the foot bearing weight on the insole. Thus, the material of the insole may be selected to have the flexibility, density, and/or compressibility to transfer the support from the underside of the insole to the foot. The portions of the insole without the orthopedic pads may be relatively uniform in thickness, though it is also understood that there may also be a gradient in thickness with the insole at the forefront of the foot having a lesser thickness than at the heel of the foot. The orthopedic pads 31 may have a height of at least 1 mm above the surrounding portions of the insole. In other embodiments, it may be at least 2 mm, 3 mm, or 5 mm, such as up to 30 mm. Further, it is also understood that the pads do not have to have a uniform height (in a given region or between pads). Rather, a pad may have a contoured upper surface that provides a transition from the substantially flat bottom portion into the shape of the pad. Further, it is also understood that a single pad may extend between multiple regions of the foot, for example, a single pad may extend between both the medial longitudinal arch and the lateral longitudinal arch. Further, a single pad may extend between all of the medial longitudinal arch, the lateral longitudinal arch, and the transverse metatarsal arch. When a pad extends between multiple regions, it may have a reduced height between regions of peak heights. For example, in a pad that extends across a region corresponding to both the medial longitudinal arch and the lateral longitudinal arch, the pad may have a first peak height at a location corresponding to the medial longitudinal arch, a second peak height at a location corresponding to the lateral longitudinal arch, and a third peak height at the transverse arch. The first peak height is greater than the second peak height, which is greater than the third peak height. Further, it as illustrated in FIGS. 2-7, the insole may extend laterally beyond the sole of the shoe in which it will be placed, forming wings 36. When the insole and foot are placed in the shoe together, the wings 36 may wrap up the side of the foot. This may be particularly desirable adjacent the medial longitudinal arch and the lateral longitudinal arch.

In FIGS. 3-4, there are one or more recessed regions formed on the bottom portion of the insole that may be optionally included. That is, the bottom portion may have regions that are thinner than the remaining portions of the insole, which as shown in FIGS. 3-4, may be referred to as recessed regions 34 and 35. In particular, recessed region 35 is formed at the location of a wing 36, and may reduce the amount of the material wrapping around the foot. The groove 34 may be placed under the second to fifth toes to provide greater room and flexibility for the toes when one is walking on the orthopedic insole.

Further in FIGS. 3-4, there are one or more grooves formed on the one or more orthopedic pads. In this example, grooves 33 are formed on orthopedic pad 31 (being in the region of the arches, as described above). Specifically, grooves 33 may extend longitudinally along each of the medial longitudinal arch and the lateral longitudinal arch. As shown, there are a plurality of substantially parallel grooves 33 at the location corresponding to the medial longitudinal arch and the lateral longitudinal arch. These grooves provide flexibility allowing the insole to interface with foot wear and easily contour to the footwear. The present design allows the insole to support the foot when it is most essential and then to recoil and move away from the foot when the support is not as necessary. This cannot be accomplished with rigid materials and a flexible material with recoil will effectively allow this to occur.

Referring now to FIGS. 8-11, another embodiment of an insole is shown. FIG. 8 shows a bottom side of the insole, FIG. 9 shows an isometric view of the bottom side, FIG. 10 shows a rear view (from perspective of heel towards toe), and FIG. 11 shows a front view (from perspective of toe towards heel). As shown, insole 20 includes several orthopedic shaped pads at selected locations disposed on the bottom portion 30 of the insole 20. As shown, in this example, there are two orthopedic pads: the orthopedic pad 31 disposed at the location under an arch, and the orthopedic pad 32 disposed at the location under a big toe. Pads 31 and 32 extend a height away from the bottom surface of the insole 20 (i.e., the surface that does not interface a foot but instead interfaces a shoe). Pad 31 may be contoured to have distinct peaks corresponding to each of the lateral arch, medial arch, and transverse arch, where the portion of pad 31 corresponding to the medial arch may have the greatest height, the portion of pad 31 corresponding to the lateral arch may have the second greatest height, and the portion of pad 31 corresponding to the transverse arch may have the smallest height (of the three arches). Further, contouring between each of these arches exists to provide a smooth transition therebetween. The insole 20 may extend laterally beyond the sole of the shoe in which it will be placed, forming wings 36. When the insole 20 and foot are placed in the shoe together, the wings 36 may wrap up the side of the foot. However, the wings 36 may be formed with a smooth transition to the portion of the insole corresponding to the forefront of the foot (in contrast to the prior embodiments which show a cusp on the lateral side of the insole and a smooth transition on the medial side of the insole). As shown, the wraps are not symmetrical (but may be in other embodiments). Further, the pad 31 extends into wings 36, and as shown, the pad 31 under the medial arch may be longer than the reach under the lateral arch.

An orthopedic pad 38 under the heel (i.e., heel plugs or heel lifts) may elevate the heel of the foot to allow for less strain of the Achilles tendon and plantar fascia. Such pad 38 may have a height that is substantially similar to the height of the pad 31 under the transverse arch, but may also be greater or less than the transverse arch in other embodiments. Unlike the prior embodiments, pad 32 under the big toe is used without a recessed region or groove under the second to fifth toes, and pad 31 is used without recessed regions in the transition area between wings 36 and the portion of the insole that interfaces the bottom surface of the foot, when the wings 36 wrap around (or up the side of) the foot.

While the invention has been described with respect to a limited number of embodiments, those skilled in the art, having the benefit of this disclosure, will appreciate that other embodiments that do not depart from the scope of the invention as disclosed herein can be devised. Accordingly, the scope of the invention should not be limited only by the attached claims.

What is claimed:

1. An orthopedic insole, comprising:
    an insole having a baseline thickness, a bottom portion of which is configured to face a sole of a shoe;
    one unitary orthopedic pad fixed on and extending away from the baseline thickness at the bottom portion of the insole at a location in a middle region configured to be under and support as a unitary structure a medial longitudinal arch, a lateral longitudinal arch and a transverse arch, and optionally one or more orthopedic pads at one or more locations selected from the group consisting of a location in a distal region configured to be under a big toe, a location in the distal region configured to be under second and third metatarsals, and fourth and fifth metatarsals, and a location in a proximal region configured to be under a heel; and
    a first convex wing extending outwards from the middle region adjacent the location in the middle region configured to be under the medial longitudinal arch and a second convex wing extending outwards from the middle region adjacent the location in the middle region configured to be under the lateral longitudinal arch, wherein the one unitary orthopedic pad is configured to be under the medial longitudinal arch, the lateral longitudinal arch, and the transverse arch extends onto the first and second convex wings,
    wherein the one unitary orthopedic pad has a peak thickness above the baseline thickness in an interior portion of the orthopedic pad configured to be under the medial longitudinal arch and tapers to the baseline thickness at the first and second convex wing and at a distal end of the middle region adjacent the location configured to be under the transverse arch; and
    wherein the one unitary orthopedic pad has a medial longitudinal arch peak, a lateral longitudinal arch peak, and a transverse arch peak, wherein the one unitary orthopedic pad has a reduced height between each peak, wherein the reduced height extends above the baseline thickness.

2. The orthopedic insole of claim 1, wherein the one unitary orthopedic pad is at a height of at least 1 mm above other regions of the bottom portion of the insole.

3. The orthopedic insole of claim 1, wherein the one unitary orthopedic pad is configured to provide different flexibility than another portion of the orthopedic insole.

4. The orthopedic insole of claim 1, wherein the one unitary orthopedic pad is made of different materials with different properties than another portion of the orthopedic insole.

5. The orthopedic insole of claim 1, wherein the one unitary orthopedic pad has contoured surfaces.

6. The orthopedic insole of claim 5, wherein the one unitary orthopedic pad has contouring between peaks at regions corresponding to the medial longitudinal arch, the lateral longitudinal arch, and the transverse arch.

7. The orthopedic insole of claim 1, wherein the one unitary orthopedic pad at the middle region, configured to correspond to the medial longitudinal arch, is greater in height than the one unitary orthopedic pad at the middle region, configured to correspond to the lateral longitudinal arch, which is greater in height than the one unitary orthopedic pad at the middle region, configured to correspond to the transverse metatarsal arch.

8. The orthopedic insole of claim 1:
wherein the one unitary orthopedic pad extends furthest towards a region configured to be under the toes at a proximal region of the toes configured to correspond to the transverse metatarsal arch, second furthest towards the region configured to be under the toes at the middle region configured to be under the medial longitudinal arch, and third furthest towards the region configured to be under the toes at the middle region configured to be under the lateral longitudinal arch.

9. The orthopedic insole of claim 8, wherein the first orthopedic pad has:
a first peak height at a location configured to correspond to the medial longitudinal arch, and
a second peak height at a location configured to correspond to the lateral longitudinal arch;
the first peak height being greater than the second peak height.

10. The orthopedic insole of claim 8, wherein the first convex wing and the second convex wing are configured to extend laterally beyond a sole of a shoe in which the insole is to be placed, when not in a shoe, and to wrap up a side of a foot adjacent to the medial longitudinal arch and/or the lateral longitudinal arch, when placed in a shoe.

11. The orthopedic insole of claim 8, further comprising:
a second orthopedic pad disposed on the bottom portion of the insole at a location corresponding to a big toe of the foot.

12. The orthopedic insole of claim 8, further comprising:
a second orthopedic pad disposed on a top portion of the insole at a location corresponding to a big toe of the foot.

13. A shoe, comprising:
an upper;
a sole attached to the upper, and
a removable insole within the shoe, the removable insole being the orthopedic insole of claim 1.

14. The orthopedic insole of claim 1, wherein the orthopedic insole is configured to dynamically support a foot during ambulation, thereby providing a change in contact between the foot and the medial longitudinal arch, the lateral longitudinal arch and/or the transverse arch, such that when a heel lifts off the ground, the one unitary orthopedic pad reduces contact with the medial longitudinal arch, the lateral longitudinal arch and/or the transverse arch.

15. The orthopedic insole of claim 1, wherein the first convex wing and the second convex wing are configured to extend laterally beyond a sole of a shoe in which the insole is to be placed, when not in a shoe, and to wrap up a side of a foot adjacent to the medial longitudinal arch and/or the lateral longitudinal arch, when placed in the shoe.

16. The orthopedic insole of claim 1, wherein the material of the insole is selected to have the flexibility, density, and/or compressibility configured to transfer support of the one unitary orthopedic pad from the bottom portion of the insole to a foot when weight is applied to the insole.

17. An orthopedic insole, comprising:
an insole having a baseline thickness, a bottom portion of which is configured to face a sole of a shoe;
one unitary orthopedic pad fixed on and extending away from the baseline thickness at the bottom portion of the insole at a location in a middle region configured to be under and support as a unitary structure a medial longitudinal arch, a lateral longitudinal arch and a transverse arch, and optionally one or more orthopedic pads at one or more locations selected from the group consisting of a location in a distal region configured to be under a big toe, a location in the distal region configured to be under second and third metatarsals, and fourth and fifth metatarsals, and a location in a proximal region configured to be under a heel; and
a first convex wing extending outwards from the middle region adjacent the location in the middle region configured to be under the medial longitudinal arch and a second convex wing extending outwards from the middle region adjacent the location in the middle region configured to be under the lateral longitudinal arch, wherein the one unitary orthopedic pad configured to be under a medial longitudinal arch, a lateral longitudinal arch, and a transverse arch extends onto the first and second convex wings,
wherein the one unitary orthopedic pad has a peak thickness above the baseline thickness in an interior portion of the orthopedic pad configured to be under the medial longitudinal arch and tapers to the baseline thickness at the first and second convex wing and at a distal end of the middle region adjacent the location configured to be under the transverse arch;
wherein the one unitary orthopedic pad at the middle region, configured to correspond to the medial longitudinal arch, is greater in height than the one unitary orthopedic pad at the middle region, configured to correspond to the lateral longitudinal arch, which is greater in height than the one unitary orthopedic pad at the middle region, configured to correspond to the transverse metatarsal arch; and
wherein the height of the pad between the one unitary orthopedic pad at the middle region, configured to correspond to the medial longitudinal arch, the one unitary orthopedic pad at the middle region, configured to correspond to the lateral longitudinal arch and the one unitary orthopedic pad at the middle region, configured to correspond to the transverse metatarsal arch extends above the baseline thickness.

* * * * *